United States Patent [19]

Masumoto et al.

[11] Patent Number: 5,498,792
[45] Date of Patent: Mar. 12, 1996

[54] PROCESS OF PRODUCING N-ALKYLACETAMIDES

[75] Inventors: Katuhisa Masumoto, Ibaraki; Akihiko Nakamura, Takatsuki; Yujiro Kiyoshima, Oita; Mikio Sasaki; Asako Tanahashi, both of Ibaraki, all of Japan

[73] Assignees: Shionogi & Co., Ltd.; Sumitomo Chemical Co., Ltd., both of Osaka, Japan

[21] Appl. No.: 305,923

[22] Filed: Sep. 16, 1994

[30] Foreign Application Priority Data

Sep. 16, 1993 [JP] Japan .................... 5-230002

[51] Int. Cl.⁶ .................... C07C 233/05; C07C 231/06
[52] U.S. Cl. .................... 564/164; 564/147; 564/124; 564/163; 564/165; 564/171; 564/244
[58] Field of Search .................... 564/147, 244, 564/124, 165, 171, 162, 163, 164, 169

[56] References Cited

FOREIGN PATENT DOCUMENTS 1264944  2/1972  United Kingdom .................... 564/246

OTHER PUBLICATIONS

Dox et al. *Organic Structures* vol. 1 (p. 5), 1941.
Schaefer et al. (1962) J. Org. Chem. vol. 27 (1255–58).
Annalen der Chemie 265 Bd. (156–158) w/translation, 1891.

*Primary Examiner*—Shailendra Kumar
*Attorney, Agent, or Firm*—Birch, Stewart, Kolasch and Birch

[57] ABSTRACT

There is disclosed a process of producing an N-alkylacetamide of the general formula (III):

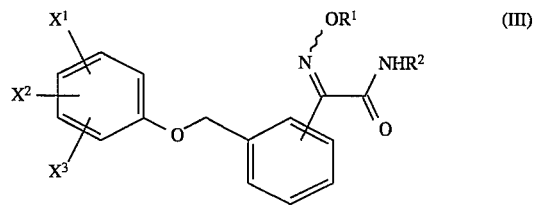

wherein $X^1$, $X^2$ and $X^3$ are the same or different and are independently hydrogen, lower alkyl, lower alkoxy, lower alkenyl, halogen or trifluoromethyl; $R^1$ and $R^2$ are the same or different and are independently lower alkyl; and $\sim$ represents a chemical bond of E- or Z-configuration, or a mixture of these configurations, which includes the steps of:

(a) reacting an acetonitrile of the general formula (I):

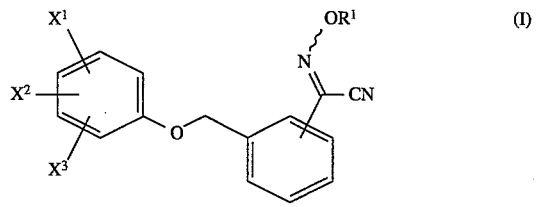

wherein $X^1$, $X^2$, $X^3$, $R^1$ and $\sim$ are each as defined above, with an alkylamine of the general formula (IV):

$$R^2-NH_2 \qquad (IV)$$

wherein $R^2$ is as defined above, to give an N-alkylacetamidine of the general formula (II):

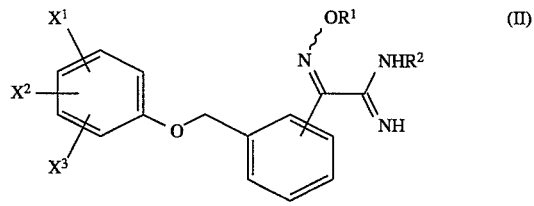

wherein $X^1$, $X^2$, $X^3$, $R^1$, $R^2$ and $\sim$ are each as defined above; and (b) reacting the N-alkylacetamidine (II) with a nitrite derivative in the presence of an acid.

12 Claims, No Drawings

PROCESS OF PRODUCING N-ALKYLACETAMIDES

FIELD OF THE INVENTION

The present invention relates to a process of producing certain kinds of N-alkylacetamides which are useful as bactericides or fungicides for agricultural use.

BACKGROUND OF THE INVENTION

It is well known that N-alkylacetamides of the general formula (III):

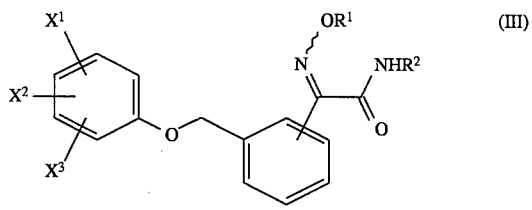

wherein $X^1$, $X^2$ and $X^3$ are the same or different and are independently hydrogen, lower alkyl, lower alkoxy, lower alkenyl, halogen or trifluoromethyl; $R^1$ and $R^2$ are the same or different and are independently lower alkyl; and ∼∼ represents a chemical bond of E- or Z- configuration, or a mixture of these configurations, are useful as bactericides or fungicides for agricultural use. A process for their production is disclosed in the Japanese Patent Laid-open Publication No. 288045/1992. In this process, a certain acetonitrile compound (I) is hydrolyzed into the corresponding acetamide (II), which is then reacted with an alkylating agent in the presence of a base, as shown in the reaction scheme:

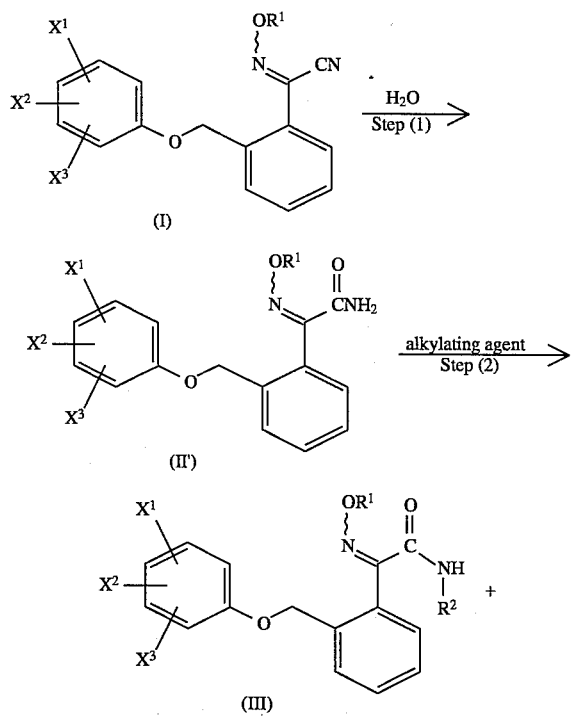

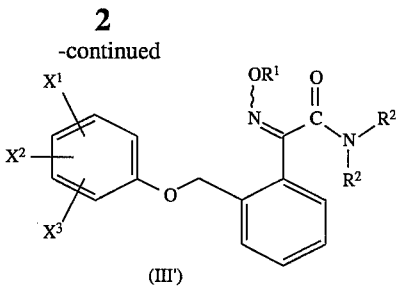

wherein $X^1$, $X^2$, $X^3$, $R^1$, $R^2$ and ∼∼ are each as defined above.

The above process, however, has serious disadvantages that the yield of the acetamide (II') as an intermediate is as low as about 70% and that the desired compound is only obtained in as low yield as about 50% because the N,N-dialkyl product (III') is formed as a by-product through the reaction of the intermediate and the alkylating agent.

Accordingly, there is a great demand for the development of a process of producing an N-alkylacetamide as the desired compound in high yield without going through the above intermediate.

SUMMARY OF THE INVENTION

Under these circumstances, the present inventors have intensively studied to find a process of producing an N-alkylacetamide of the general formula (III) in high yield, which can solve the above disadvantages. As the result, they have found that the initial reaction of a particular acetonitrile compound with an alkylamine to give an N-alkylacetamidine as an intermediate and the subsequent reaction of the intermediate with a nitrite derivative can provide the desired N-alkylacetamide in high yield, thereby completing the present invention.

Thus, the present invention provides a process of producing an N-alkylacetamide of the general formula (III):

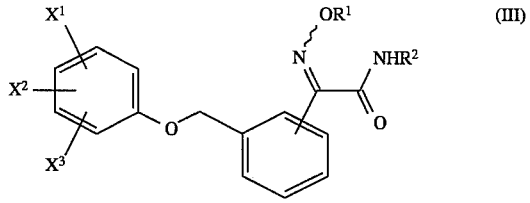

wherein $X^1$, $X^2$ and $X^3$ are the same or different and are independently hydrogen, lower alkyl, lower alkoxy, lower alkenyl, halogen or trifluoromethyl; $R^1$ and $R^2$ are the same or different and are independently lower alkyl; and ∼∼ represents a chemical bond of E- or Z-configuration, or a mixture of these configurations, which comprises the steps of:

(a) reacting an acetonitrile of the general formula (I):

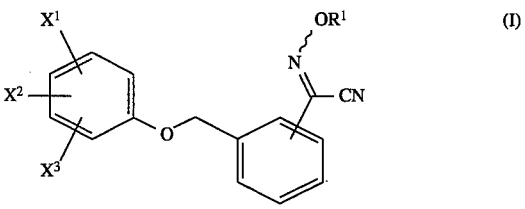

wherein $X^1$, $X^2$, $X^3$, $R^1$ and ∼∼ are each as defined above, with an alkylamine of the general formula (IV):

$$R^2\text{—}NH_2 \qquad (IV)$$

wherein $R^2$ is as defined above, to give an N-alkylacetamidine of the general formula (II):

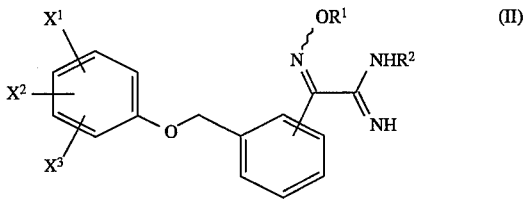

wherein $X^1$, $X^2$, $X^3$, $R^1$, $R^2$ and ∿ represents a chemical bond of E- or Z-configuration, or a mixture of these configurations, are each as defined above; and (b) reacting the N-alkylacetamidine (II) with a nitrite derivative in the presence of an acid.

DETAILED DESCRIPTION OF THE INVENTION

The following will describe the step (a) in which the acetonitrile (I) is reacted with the alkylamine (IV) to give the N-alkylacetamidine (II).

In the acetonitrile (I), the substituents $X^1$, $X^2$ and $X^3$ are the same or different and are independently hydrogen; straight-chain or branched lower alkyl containing 1 to 5 carbon atoms, such as methyl, ethyl, propyl, isopropyl, butyl, sec-butyl, tert-butyl, amyl or tert-amyl; straight-chain or branched lower alkoxy containing 1 to 5 carbon atoms, such as methoxy, ethoxy, propoxy or butoxy; straight-chain or branched lower alkenyl containing 2 to 4 carbon atoms, such as ethenyl, propenyl or butenyl; halogen such as fluorine, chlorine or bromine; or trifluoromethyl.

The substituent $R^1$ is straight-chain or branched lower alkyl containing 1 to 5 carbon atoms, such as methyl, ethyl, propyl, isopropyl, butyl, sec-butyl, tert-butyl, amyl or tert-amyl.

Examples of the acetonitrile (I) are α-methoxyimino-2-phenoxymethyl-phenylacetonitrile, α-methoxyimino-2-(2-methylphenoxymethyl)phenylacetonitrile, α-methoxyimino-2-(3-methylphenoxymethyl)phenylacetonitrile, α-methoxyimino-2-(4-methylphenoxymethyl)phenylacetonitrile, α-methoxyimino-2-(2-ethylphenoxymethyl)phenylacetonitrile, α-methoxyimino-2-(2-propylphenoxymethyl)phenylacetonitrile, α-methoxyimino-2-(2-isopropylphenoxymethyl)phenylacetonitrile, α-methoxyimino-2-(2-butylphenoxymethyl)phenylacetonitrile, α-methoxyimino-2-(2-amylphenoxymethyl)phenylacetonitrille, α-methoxyimino-2-(2,3-dimethylphenoxymethyl)phenylacetonitrile, α-methoxyimino-2-(2,4-dimethylphenoxymethyl)phenylacetonitrile, α-methoxyimino-2-(2,5-dimethylphenoxymethyl)phenylacetonitrile, α-methoxyimino-2-(2,6-dimethylphenoxymethyl)phenylacetonitrile, α-methoxyimino-2-(3,4-dimethylphenoxymethyl)phenylacetonitrile, α-methoxyimino-2-(3,5-dimethylphenoxymethyl)phenylacetonitrile, α-methoxyimino-2-(2-fluorophenoxymethyl)phenylacetonitrile, α-methoxyimino-2-(3-fluorophenoxymethyl)phenylacetonitrile, α-methoxyimino-2-(4-fluorophenoxymethyl)phenylacetonitrile, α-methoxyimino-2-(2-chlorophenoxymethyl)phenylacetonitrile, α-methoxyimino-2-(2,4-difluorophenoxymethyl)phenylacetonitrile, α-methoxyimino-2-(2,4-dichlorophenoxymethyl)phenylacetonitrile, α-methoxyimino-2-(3-chloro-4-fluorophenoxymethyl)phenylacetonitrile, α-methoxyimino-2-(4-chloro-2-methylphenoxymethyl)phenylacetonitrile, α-methoxyimino-2-(2-fluoro-6-methoxyphenoxymethyl)phenylacetonitrile, α-methoxyimino-2-(2-trifluoromethylphenoxymethyl)phenylacetonitrile, α-methoxyimino-2-(3-trifluoromethylphenoxymethyl)phenylacetonitrile, α-methoxyimino-2-(4-trifluoromethylphenoxymethyl)phenylacetonitrile, α-ethoxyimino-2-phenoxymethylphenylacetonitrile, α-ethoxyimino-2-(2-methylphenoxymethyl)phenylacetonitrile, α-ethoxyimino-2-(2,5-dimethylphenoxymethyl)phenylacetonitrile, α-ethoxyimino-2-(4-chloro-2-methylphenoxymethyl)phenylacetonitrile and α-ethoxyimino-2-(3-trifluoromethylphenoxymethyl)phenylacetonitrile.

In the alkylamine (IV), the substituent $R^2$ may be straight-chain or branched lower alkyl containing 1 to 5 carbon atoms, which is, for example, the same as defined for the substituent $R^1$. The substituents $R^1$ and $R^2$ are the same or different from each other.

Examples of the alkylamine (IV) are methylamine, ethylamine, propylamine, butylamine and amylamine.

The amount of the alkylamine (IV) to be used is usually in the range of 0.8 to 20 moles, preferably 1.2 to 6 moles, per mole of the acetonitrile (I).

The acetonitrile (I) and the alkyl amine (IV) are usually reacted in the presence of a solvent which is substantially inert to this reaction. Examples of the solvent are alcohols such as methanol, ethanol, propanol, isopropanol and butanol; aromatic hydrocarbons such as benzene, toluene and xylene; halogenated hydrocarbons such as chlorobenzene and o-dichlorobenzene; and ethers such as tetrahydrofuran and dioxane. These solvents may be used alone or in combination.

The amount by weight of the solvent to be used is usually in the range of about 1 to 20 times the weight of the acetonitrile (I).

The reaction is usually effected at a temperature of 0° to 200° C., preferably 50° to 160° C., for a period of about 0.5 to 30 hours.

The reaction may be effected in the presence of a catalyst. Examples of the catalyst are metal alkoxides such as sodium methoxide, sodium ethoxide and potassium t-butoxide; and organic bases such as 1,8-diazabicyclo[5.4.0]undec-7-ene and 1,4-diazabicyclo[2.2.2]octane.

The amount of the catalyst to be used is usually in the range of 0.005 to 1 mole, preferably 0.01 to 0.3 mole, per mole of the acetonitrile (I).

Thus, a reaction mixture containing the N-alkylacetamidine (II) can be obtained. The reaction mixture is concentrated and then made acidic with the addition of an acid such as diluted hydrochloric acid, to which a water-insoluble organic solvent selected from the same aromatic hydrocarbons, halogenated hydrocarbons and ethers as described above is added to extract impurities into an organic layer which is then separated and removed, thereby obtaining an acid addition salt of the N-alkylacetamidine (II) in the form of an aqueous solution.

The aqueous solution of the acid addition salt can be used as such in the subsequent step, or when the product is to be isolated, for example, the aqueous solution is made basic with the addition of a base such as sodium hydroxide and extracted with the same water-insoluble organic solvent as described above. The aqueous layer is separated and removed, and the organic layer is concentrated to give the N-alkylacetamidine (II) in the form of an isolated product.

The N-alkylacetamidine (II) can also be isolated by a method in which a water insoluble organic solvent selected from the same aromatic hydrocarbons, halogenated hydrocarbons and ethers as described above is added to the reaction mixture or the concentrate of this mixture and after separation and removal of the aqueous layer the solvent is distilled off.

The following will describe the step (b) in which the N-alkylacetamidine (II) is reacted with a nitrite derivative in the presence of an acid to give the N-alkylacetamide (III).

Examples of the nitrite derivative are sodium nitrite, potassium nitrite, nitrosyl chloride, nitrosylsulfuric acid, methyl nitrite, ethyl nitrite, n-propyl nitrite, isopropyl nitrite, n-butyl nitrite, amyl nitrite, hexyl nitrite, dinitrogen trioxide and nitrogen monoxide-oxygen mixtures. Preferred is sodium nitrite.

The nitrite derivative may be synthesized by a known method or available from any commercial source.

The amount of the nitrite derivative to be used is usually in the range of 0.8 to 30 moles, preferably 1 to 8 moles, per mole of the N-alkylacetamidine (II).

The reaction is usually effected in the presence of an acid. Examples of the acid are inorganic acids such as hydrochloric acid, sulfuric acid and phosphoric acid; and organic acids such as formic acid, acetic acid, trifluoroacetic acid, methanesulfonic acid, p-toluenesulfonic acid, acetic anhydride and trifluoroacetic anhydride. These acids may be used alone or in combination.

The amount of the acid to be used is usually in the range of 0.8 to 30 moles, preferably 1 to 15 moles, per mole of the N-alkylacetamidine (II).

The reaction is usually effected in the presence of a solvent. Examples of the solvent are alcohols such as methanol, ethanol, propanol, isopropanol and butanol; aromatic hydrocarbons such as benzene, toluene and xylene; halogenated hydrocarbons such as chlorobenzene and o-dichlorobenzene; and ethers such as tetrahydrofuran and dioxane. These solvents may be used alone or in combination.

The amount by weight of the solvent to be used is usually in the range of about 1 to 20 times the weight of the N-alkylacetamidine (II).

The reaction is usually effected in the presence of an acid at a temperature of 0° to 100° C., preferably 30° to 70° C., for a period of about 1 to 150 hours.

Thus, a reaction mixture containing the N-alkylacetamide (III) as the desired compound is obtained. If necessary, the desired compound may be isolated by the following method. For example, the reaction mixture is adjusted to pH 12 or higher with the addition of a base, and if necessary, the mixture is neutralized, to which a water insoluble organic solvent selected from the same aromatic hydrocarbons, halogenated hydrocarbons and ethers as described above is added to extract the desired compound, after which the aqueous layer is separated and removed and the organic layer is washed and concentrated.

Examples of the base are alkylamines such as methylamine and ethylamine; and inorganic bases such as sodium hydroxides.

Examples of the N-alkylacetamide (III) are α-methoxyimino-2-phenoxymethylphenyl-N-methylacetamide, α-methoxyimino-2-( 2-methylphenoxymethyl)phenyl-N-methylacetamide, α-methoxyimino-2-(3-methylphenoxymethyl)phenyl-N-methylacetamide, α-methoxyimino-2-(4-methylphenoxymethyl)phenyl-N-methylacetamide, α-methoxyimino-2-(2-ethylphenoxymethyl)phenyl-N-methylacetamide, α-methoxyimino-2-(2-propylphenoxymethyl)phenyl-N-methylacetamide, α-methoxyimino-2-(2-isopropylphenoxymethyl)phenyl-N-methylacetamide, α-methoxyimino-2-(2-butylphenoxymethyl)phenyl-N-methylacetamide, α-methoxyimino-2-(2-amylphenoxymethyl)phenyl-N-methylacetamide, α-methoxyimino-2-(2,3-dimethylphenoxymethyl)phenyl-N-methylacetamide, α-methoxyimino-2-(2,4-dimethylphenoxymethyl)phenyl-N-methylacetamide, α-methoxyimino-2-(2,5-dimethylphenoxymethyl)phenyl-N-methylacetamide, α-methoxyimino-2-(2,6-dimethylphenoxymethyl)phenyl-N-methylacetamide, α-methoxyimino-2-(3,4-dimethylphenoxymethyl)phenyl-N-methylacetamide, α-methoxyimino-2-(3,5-dimethylphenoxymethyl)phenyl-N-methylacetamide, α-methoxyimino-2-(2-fluorophenoxymethyl)phenyl-N-methylacetamide, α-methoxyimino-2-(3-fluorophenoxymethyl)phenyl-N-methylacetamide, α-methoxyimino-2-(4-fluorophenoxymethyl)phenyl-N-methylacetamide, α-methoxyimino-2-(2-chlorophenoxymethyl)phenyl-N-methylacetamide, α-methoxyimino-2-(2,4-difluorophenoxymethyl)phenyl-N-methylacetamide, α-methoxyimino-2-(2,4-dichlorophenoxymethyl)phenyl-N-methylacetamide, α-methoxyimino-2-(3-chloro-4-fluorophenoxymethyl)phenyl-N-methylacetamide, α-methoxyimino-2-(4-chloro-2-methylphenoxymethyl)phenyl-N-methylacetamide, α-methoxyimino-2-(2-fluoro-6-methoxyphenoxymethyl)phenyl-N-methylacetamide, α-methoxyimino-2-(2-trifluoromethylphenoxymethyl)phenyl-N-methylacetamide, α-methoxyimino-2-(3-trifluoromethylphenoxymethyl)phenyl-N-methylacetamide, α-methoxyimino-2-(4-trifluoromethylphenoxymethyl)phenyl-N-methylacetamide, α-ethoxyimino-2-phenoxymethylphenyl-N-methylacetamide, α-ethoxyimino-2-(2-methylphenoxymethyl)phenyl-N-methylacetamide, α-ethoxyimino-2-(2,5-dimethylphenoxymethyl)phenyl-N-methylacetamide, α-ethoxyimino-2-(4-chloro-2-methylphenoxymethyl)phenyl-N-methylacetamide, α-ethoxyimino-2-(3-trifluoromethylphenoxymethyl)phenyl-N-methylacetamide, α-methoxyimino-2-phenoxymethylphenyl-N-ethylacetamide, α-methoxyimino-2-(2-methylphenoxymethyl)phenyl-N-ethylacetamide, α-methoxyimino-2-(3-methylphenoxymethyl)phenyl-N-ethylacetamide, α-methoxyimino-2-(4-methylphenoxymethyl)phenyl-N-ethylacetamide, α-methoxyimino-2-(2-ethylphenoxymethyl)phenyl-N-ethylacetamide, α-methoxyimino-2-(2-propylphenoxymethyl)phenyl-N-ethylacetamide, α-methoxyimino-2-(2-isopropylphenoxymethyl)phenyl-N-ethylacetamide, α-methoxyimino-2-(2-butylphenoxymethyl)phenyl-N-ethylacetamide, α-methoxyimino-2-(2-amylphenoxymethyl)phenyl-N-ethylacetamide, α-methoxyimino-2-(2,3-dimethylphenoxymethyl)phenyl-N-ethylacetamide, α-methoxyimino-2-(2,4-dimethylphenoxymethyl)phenyl-N-ethylacetamide, α-methoxyimino-2-(2,5-dimethylphenoxymethyl)phenyl-N-ethylacetamide, α-methoxyimino-2-(2,6-dimethylphenoxymethyl)phenyl-N-ethylacetamide, α-methoxyimino-2-(3,4-dimethylphenoxymethyl)phenyl-N-ethylacetamide, α-methoxyimino-2-(3,5-dimethylphenoxymethyl)phenyl-N-ethylacetamide, α-methoxyimino-2-(2-fluorophenoxymethyl)phenyl-N-ethylacetamide, α-methoxyimino-2-(3-fluorophenoxymethyl)phenyl-N-ethylacetamide, α-methoxyimino-2-(4-fluorophenoxymethyl)phenyl-N-ethylacetamide, α-methoxyimino-2-(2-chlorophenoxymethyl)phenyl-N-ethylacetamide, α-methoxyimino-2-(2,4-difluorophenoxymethyl)phenyl-N-ethylacetamide, α-methoxyimino-2-(2,4-dichlorophenoxymethyl)phenyl-N-ethylacetamide, α-methoxyimino-2-(3-chloro-4-fluorophenoxymethyl)phenyl-N-ethylacetamide, α-methoxyimino-2-(4-chloro-2-methylphenoxymethyl)phenyl-N- ethylacetamide, α-methoxyimino-2-(2-fluoro-6-methoxyphenoxymethyl)phenyl-N-ethylacetamide, α-methoxyimino-2-(2-trifluoromethylphenoxymethyl)phenyl-N-ethylacetamide, α-methoxyimino-2-(3-trifluoromethylphenoxymethyl)phenyl-N-ethylacetamide, α-methoxyimino-2-(4-trifluoromethylphenoxymethyl)phenyl-N-ethylacetamide, α-ethoxyimino-2-phenoxymethylphenyl-N-ethylacetamide, α-ethoxyimino-2-(2-methylphenoxymethyl)phenyl-N-ethylacetamide, α-ethoxyimino-2-(2,5-dimethylphenoxymethyl)phenyl-N-ethylacetamide, α-ethoxyimino-2-(4-chloro-2-methylphenoxyphenyl-N-ethylacetamide and α-ethoxyimino-2-(3-trifluoromethylphenoxmethyl)phenyl-N-ethylacetamide.

The N-alkylacetamide (III) is usually obtained in an isomer mixture of the E and Z forms. The Z form can readily be isomerized into the E form by the addition of an acid usually in the presence of a solvent.

As the acid which can be used in the isomerization, for example, there can be mentioned hydrohalogenic acids, hydrogen halides, sulfonic acids and acid addition salts of organic bases.

Examples of the hydrohalogenic acid are hydrochloric acid, hydrobromic acid and hydroiodic acid. Examples of the hydrogen halide are hydrogen chloride, hydrogen bromide and hydrogen iodide. Examples of the sulfonic acid are aliphatic sulfonic acids such as trifluoromethanesulfonic acid; and aromatic sulfonic acids such as toluenesulfonic acid. Examples of the acid addition salt of organic bases are hydrohalogenic acid addition salts of organic bases, wherein examples of the hydrohalogenic acid are hydrochloric acid and hydrobromic acid and examples of the organic base are aliphatic amines such as methylamine and triethylamine; alkoxyamines such as methoxyamine, ethoxy amine, propoxyamine and butoxyamine; hydroxylamine; aromatic amines such as aniline; and heterocyclic amines such as pyridine.

The amount of the acid to be used is usually in the range of 0.005 to 20 moles, preferably 0.05 to 3 moles, per mole of the N-alkylacetamide (III) (as an isomer mixture of the E and Z forms).

Examples of the solvent are aromatic hydrocarbons such as benzene, toluene and xylene; halogenated hydrocarbons such as methylene chloride, 1,2-dichloroethane, chlorobenzene and o-dichlorobenzene; ethers such as tetrahydrofuran and dioxane; ketones such as acetone, methyl ethyl ketone and methyl isobutyl ketone; and water. These solvents may be used alone or in combination.

The amount by weight of the solvent to be used is usually in the range of about 1 to 50 times the weight of the N-alkylacetamide (III) (as an isomer mixture of the E and Z forms).

The isomerization is usually effected at a temperature of 0° to 180° C., prefer ably 20° to 140° C. for a period of 10 minutes to 200 hours, preferably 30 minutes to 150 hours.

The E form thus obtained, (E)-N-alkylacetamide, can be isolated by ordinary procedures such as extraction, separation, water washing and concentration, if necessary. Further, it can be purified by a technique such as column chromatography or recrystallization.

The present invention will be further illustrated by the following examples, which are not to be construed to limit the scope thereof.

EXAMPLE 1

In a stainless steel autoclave were charged 14.7 g (50 mmol) of α-methoxyimino-2-(2,5-dimethylphenoxymethyl)phenylacetonitrile, 7.5 ml of methanol, 0.76 g (5.0 mmol) of 1,8-diazabicyclo[5.4.0]undec-7-ene and 25.9 g (250 mmol) of 30% methylamine/methanol solution. The temperature was increased to 106° C. and stirring was continued at the same temperature for 90 minutes. Then, the temperature was increased to 113° C. and stirring was continued at the same temperature for 2 hours. Further, the temperature was increased to 140° C. and stirring was continued at the same temperature for 1.5 hours. Thus, the reaction was completed.

After completion of the reaction, the autoclave was cooled to room tempera lure, and the reaction mixture was taken out and concentrated, which afforded 17.3 g of brown solid material. The analysis on high performance liquid chromatography revealed that 15.3 g (47.0 mmol) of α-methoxyimino-2-(2,5-dimethylphenoxymethyl)phenyl-N-methylacetamidine was formed and the yield was 94.0%.

Then, 1.04 g of the above brown solid material was washed with 15 ml of acetonitrile, followed by filtration. The residue was dissolved in toluene and recrystallized to give (Z)-α-methoxyimino-2-(2,5-dimethylphenoxymethyl)phenyl-N-methylacetamidine. Further, the mother liquid after the recrystallization was subjected to reverse-phase silica gel chromatography (acetonitrile: water: acetic acid=300:700:1 (v/v) as an eluent), which afforded (E)-α-methoxyimino-2-(2,5-dimethylphenoxymethyl)phenyl-N-methylacetamidine.

(Z)-α-methoxyimino-2-(2,5-dimethylphenoxymethyl)phenyl-N-methylacetamidine: mp 156°–158° C.; mass spectrum (FD-MS): M+1=326; $^1$H-NMR (CDCl$_3$/TMS) δ(ppm) 2.23 (3H, s), 2.30 (3H, s), 2.88 (3H, s), 3.99 (3H, s), 5.08 (1H, br), 5.18 (2H, s), 6.44 (1H, br), 6.66–7.67 (7H, m).

(E)-α-methoxyimino-2-(2,5-dimethylphenoxymethyl)phenyl-N-methyl acetamidine: mp 123°–125° C.; mass spectrum (FD-MS): M+1=326; $^1$H-NMR (CDCl$_3$/TMS) δ (ppm) 2.20 (3H, s), 2.28 (3H, s), 2.92 (3H, s), 3.92 (3H, s), 4.89 (2H, s), 5.56 (1H, br), 6.59–7.62 (8H, m).

EXAMPLE 2

First, 4.30 g of 75% aqueous acetic acid solution, 1.50 g of dioxane and 1.30 g (4.0 mmol) of (Z)-α-methoxyimino-2-(2,5-dimethylphenoxymethyl)phenyl-N-methylacetamidine were mixed, and to this mixture was added 4.94 g (28.0 mmol) of 39% aqueous sodium nitrite solution while keeping the temperature at 40°–45° C. over 22 hours. Stirring was continued at the same temperature for 3 hours. To the reaction mixture was added 10.0 g of 30% methylamine/methanol solution at 0°–5° C., and stirring was continued for 4 hours. The mixture was concentrated and the residue was extracted with ethyl acetate. The aqueous layer was separated and removed, and the organic layer was washed with 10% hydrochloric acid and then 10% sodium chloride solution, followed by concentration, which afforded 1.22 g of white solid material.

The analysis of the material on high performance liquid chromatography revealed that 1.13 g (3.46 mmol) of (Z)-α-methoxyimino-2-(2,5-dimethylphenoxymethyl)phenyl-N-methylacetamide was formed, and the purity and yield were 93.0% and 86.6%, respectively. The formation of (Z)-α-methoxyimino-2-(2,5-dimethylphenoxymethyl)phenyl-N,N-dimethylacetamide and (Z)-α-methoxyimino-2-(2,5-dimethylphenoxymethyl)phenylacetamide was not observed.

As described above, the process of the present invention makes it possible to produce N-alkylacetamides useful as bactericides or fungicides for agricultural use, in high yield as compared with any conventional process and without causing the formation of by-products.

What is claimed is:

1. A process of producing an N-alkylacetamide of the general formula (III):

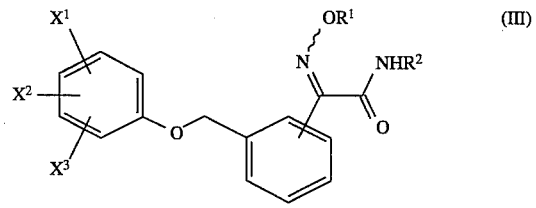

wherein $X_1$, $X_2$ and $X_3$ are the same or different and are independently hydrogen, lower alkyl, lower alkoxy, lower alkenyl, halogen or trifluoromethyl; $R^1$ and $R^2$ are the same or different and are independently lower alkyl; and ∿ represents a chemical bond of E- or Z-configuration, or a mixture of these configurations, which comprises the steps of:

(a) reacting an acetonitrile of the general formula (I):

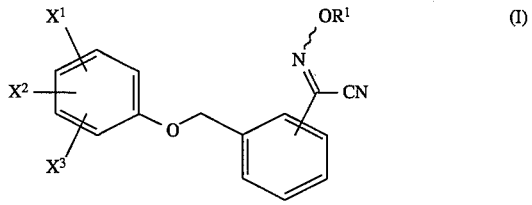

wherein $X^1$, $X^2$, $X^3$, $R^1$ and ∿ are each as defined above, with an alkylamine of the general formula (IV):

wherein $R^2$ is as defined above, and wherein the reaction of the acetontrile (I) with the alkylamine (IV) is effected in the presence of a catalyst selected from the group consisting of metal alkoxides and organic bases, to give an N-alkylacetamidine of the general formula (II):

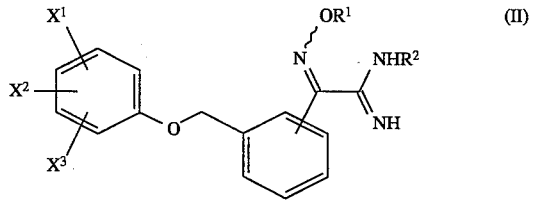

wherein $X^1$, $X^2$, $X^3$, $R^1$ and ∿ are each as defined above; and (b) reacting the N-alkylacetamidine (II) with a nitrite derivative in the presence of an acid.

2. A process according to claim 1, wherein the reaction of the acetonitrile (I) and the alkylamine (IV) is effected in the presence of a solvent.

3. A process according to claim 2, wherein the solvent is selected from the group consisting of alcohols, aromatic hydrocarbons, halogenated hydrocarbons, ethers and mixtures thereof.

4. A process according to claim 1, wherein the nitrite derivative is selected from the group consisting of sodium nitrite, potassium nitrite, nitrosyl chloride, nitrosyl-sulfuric acid, methyl nitrite, ethyl nitrite, n-propyl nitrite, isopropyl nitrite, n-butyl nitrite, amyl nitrite, hexyl nitrite, dinitrogen trioxide or nitrogen monoxide/oxygen mixtures.

5. A process according to claim 1, wherein the reaction of the N-alkylacetamidine (II) and the nitrite derivative is effected in the presence of a solvent.

6. A process according to claim 5, wherein the solvent is selected from the group consisting of alcohols, aromatic hydrocarbons, halogenated hydrocarbons, ethers, esters, water and mixtures thereof.

7. A process according to claim 1, wherein the substituents $X^1$, $X^2$ and $X^3$ are selected from the group consisting of hydrogen methyl, ethyl, propyl, isopropyl, butyl, sec-butyl, tert-butyl, amyl, tert-amyl, methoxy, ethoxy, propoxy, butoxy, ethenyl, propenyl, butenyl, fluorine, chlorine, bromine and trifluoromethyl.

8. A process according to claim 1, wherein the substituent $R^1$ is selected from the group consisting of methyl, ethyl, propyl, isopropyl, butyl, sec-butyl, tert-butyl, amyl and tert-amyl.

9. A process according to claim 1, wherein the substituent $R^2$ is selected from the group consisting of methyl, ethyl, propyl, isopropyl, butyl, sec-butyl, tert-butyl, amyl and tert-amyl.

10. A process according to claim 1, wherein the alkylamine (IV) is selected from the group consisting of methylamine, ethylamine, propylamine, butylamine and amylamine.

11. A process according to claim 1, wherein the catalyst present in the reaction of the acetonitrile (I) and the alkylamine (IV) is selected from the group consisting of sodium methoxide, sodium ethoxide, potassium t-butoxide, 1,8-diazabicyclo[5.4.0]undec-7-ene and 1,4-diazabicyclo[2.2.2] octane.

12. A process according to claim 1, wherein the acid present in the reaction of the N-alkylacetamidine (II) and the nitrite derivative is selected from the group consisting of hydrochloric acid, sulfuric acid, phophoric acid, formic acid acetic acid, trifluoroacetic acid, methanesulfonic acid, p-toluenesulfonic, acetic anhydride, trifluoroacetic anhydride and combinations thereof.

* * * * *